United States Patent [19]

Moskowitz

[11] Patent Number: 5,385,940
[45] Date of Patent: Jan. 31, 1995

[54] TREATMENT OF STROKE WITH NITRIC-OXIDE RELEASING COMPOUNDS

[75] Inventor: Michael A. Moskowitz, Belmont, Mass.

[73] Assignee: The General Hospital Corporation, Boston, Mass.

[21] Appl. No.: 972,267

[22] Filed: Nov. 5, 1992

[51] Int. Cl.⁶ .......................................... A61K 31/195
[52] U.S. Cl. ..................................................... 514/565
[58] Field of Search ................................. 514/482, 565

[56] References Cited

U.S. PATENT DOCUMENTS

| | | | |
|---|---|---|---|
| 4,152,425 | 5/1979 | Dietze et al. | 424/177 |
| 4,764,504 | 8/1988 | Johnson et al. | 514/12 |
| 4,954,526 | 9/1990 | Keefer | 514/611 |
| 4,981,691 | 1/1991 | Osterholm | 424/422 |
| 5,028,627 | 7/1991 | Kilbourn et al. | 514/565 |
| 5,039,705 | 8/1991 | Keefer et al. | 514/611 |
| 5,081,148 | 1/1992 | Braquet et al. | 514/162 |
| 5,132,453 | 7/1992 | Griffith | 562/560 |

FOREIGN PATENT DOCUMENTS

WO92/18112 10/1993 WIPO .

OTHER PUBLICATIONS

Chiacchia, K.; All About Nitric Oxide: Vital Biological Roles Revealed; Oct. 8, 1992; pp. 4–6; Focus, HMS.
Jan Koch-Weser, Drug Therapy, Dec. 24, 1981, pp. 1560–1564, N.E. Journal of Medicine.
Thompson et al., L-Arginine Increases Cerebral Blood Flow . . . , 1992, pp. 271–272, Congress of Neurological Surgeons.
Lee et al., "A Major Component of Cerebral Neurogenic Vasodilation is Mediated by Nitric Oxide", Fed. Am. Soc. Exp. Bio., 6(4): A2149 (Abstract), (1985).
Gaw et al., "Mechanism of the Endothelium–Independent Relaxation to Intraluminal Flow in a Rabbit Cerebral Artery", Fed. Am. Soc. Exp. Bio., 6(4): A2150 (Abstract), (1985).
Chen et al., "Role of Nitric Oxide in Cerebral Neurogenic Vasodilation", Fed. Am. Soc. Exp. Biol., 6(4): A1462 (Abstract), (1985).
Faraci et al., "Does Nitric Oxide Mediate Metabolic Vasodilation of the Cerebral Microcirculation?", Fed. Am. Soc. Exp. Biol., 6(4): A1462 (Conference Paper), (1985).
Iadecola et al., "Does Nitric Oxide Mediate the Cerebrovasodilation Elicited by Hypercania?", Fed. Am. Soc. Exp. Biol., 6(4): A1462 (Conference Paper), (1985).
Rosenblum, "Endothelium–Dependent L–Arg– and L–NMMA–Sensitive Mechanisms Regulate Tone of Brain Microvessels", American Physio. Soc. 1396 (1990).
Rosenblum, "L-Arginine Suffusion Restores Response to Acetylcholine in Brain Arterioles with Damaged Endothelium", American Physio. Soc., 961 (1992).
Dawson et al., "Nitric Oxide Mediates Glutamate Neurotoxicity in Primary Cortical Cultures", Proc. Natl. Acad. Sci. USA, 88:6368–6371 (1991).
Roussel et al., "Effect of MK–801 on Focal Brain Infarction in Normotensive and Hypertensive Rats", Hypertension, 19:40–46 (1992).
Nowicki et al., "Nitric Oxide Mediates Neuronal Death After Focal Cerebral Ischemia in the Mouse", Eur. J. Pharm., 204:339–340 (1991).

(List continued on next page.)

*Primary Examiner*—Raymond J. Henley, III
*Attorney, Agent, or Firm*—Wolf, Greenfield & Sacks

[57] ABSTRACT

A method for treatment of stroke in a patient, involving administering to the patient a nitric oxide-releasing compound. A preferred compound of the invention is L-arginine.

4 Claims, 3 Drawing Sheets

OTHER PUBLICATIONS

Adachi et al., "Niric Oxide (NO) is Involved in Increased Cerebral Cortical Blood Flow Following Stimulation of the Nucleus Basalis of Meynert in Anesthetized Rats", Neuroscience Ltrs., 139:201–204 (1992).

Stuehr et al., "Activated Murine Macophages Secrete a Metabolite of Arginine with the Bioactivity . . . ", J. Exp. Med., 169:1011–1020 (1989).

Sakuma et al., "Identification of Arginine as a Precursor of Endothelium-Derived Relaxing Factor", Proc. Natl. Acad. Sci. USA, 85:8664–8667 (1988).

Sloan, "Thrombolysis and Stroke", Arch Neurol., 44:748 (1987).

The Merck Manual, pp. 1330–1331, 1982.

Remington's Pharmaceutical Sciences, p. 822, 1985.

Stier et al., Dialoge Computer Data Base, Medline File, Abst. #91356323, only, of *Brain Res,* 549(2):354–6, May 1991.

*Merck Manual,* pp. 1327–1329, 1982.

Snyder, "Nitric Oxide & Neurons", Current Opinion in Neurobiology 2:323–327, 1992.

TREATMENT OF STROKE WITH NITRIC-OXIDE RELEASING COMPOUNDS

STATEMENT AS TO FEDERALLY SPONSORED RESEARCH

Studies were supported by NINCDS #NS10828 to the MGH Interdepartmental Stroke Program Project (MAM).

BACKGROUND OF THE INVENTION

This invention relates to the treatment of stroke.

Stroke occurs when a section of the brain becomes infarcted, with death of brain tissue following the interruption of cerebral blood supply. The cerebral infarcts associated with acute stroke cause sudden and dramatic neurological impairment. Stroke is the third most common cause of death in the adult population of the United States, and is a major cause of disability.

Although all body tissues are dependent upon oxygen delivered by the vasculature, the brain is so sensitive to oxygen deficit that brain cells die after only several minutes of ischemia, or impaired blood supply. Cerebral ischemia leading to stroke is caused predominantly by thrombosis, embolism or hemorrhage, with arterial blood flow blocked by blood clots, atherosclerotic plaque material, or other obstructions. The oxygen level drops in the brain tissue downstream from an occluded artery. With inadequate oxygenation, a cerebral infarct begins to form, made up of dead and dying brain tissue. Since central nervous tissue lacks the ability to regenerate, the functional capability contributed by the infarcted brain areas is permanently lost.

The infarct typically increases in size during the acute period after ischemia begins, as some of the "penumbra" tissue dies. The infarct penumbra refers to tissue which is affected by the oxygen deficit from the vessel blockage, but which receives enough oxygen from other blood vessels to maintain temporary viability. The ultimate size of the infarct, and the resultant extent of neural damage to the stroke patient, are influenced by several factors, which form the basis of medical therapy for acute stroke. Primary among these factors is the extent of vascular support for the endangered penumbra tissue.

Pharmacologic interventions have attempted to maximize the blood flow to stroke-affected brain areas which might yet be able to survive, but clinical effectiveness has proven elusive. As stated in *Harrison's Principles of Internal Medicine* (9th ed., 1980, p. 1926), "Despite experimental evidence that . . . [cerebral vasodilators] increase the cerebral blood flow, as measured by the nitrous oxide method, they have not proved beneficial in careful studies in human stroke cases at the stage of transient ischemic attacks, thrombosis-in-evolution, or in the established stroke. This is true of nicotinic acid, Priscoline, alcohol, papaverine, and inhalation of 5% carbon dioxide. . . . In opposition to the use of these methods is the suggestion that vasodilators are harmful rather than beneficial, since by lowering the systemic blood pressure they reduce the intracranial anastomotic flow, or by dilating blood vessels in the normal parts of the brain they steal blood from the infarct."

SUMMARY OF THE INVENTION

The invention features a method for treating a stroke patient by administering nitric oxide (NO) or nitric oxide-releasing compounds to the patient. Nitric oxide-releasing compounds are compounds which react within a patient's body to cause the release of free nitric oxide. Nitric oxide-releasing compounds include NO donor compounds, wherein the nitrogen released as NO is derived from nitrogen formerly covalently bound within the NO donor compound. In one preferred embodiment of the invention, the nitric oxide-releasing compound is L-arginine. L-arginine is a precursor for nitric oxide synthase, which transforms arginine into NO and citrulline. (Palmer et al., *Nature* 333:664–666, 1988). Other NO-releasing compounds included within the scope of the invention include analogs of L-arginine which are substrates for NO synthase.

In a preferred embodiment, the compounds of the invention are administered to a stroke patient. Stroke is intended to encompass conditions of neurologic deficit associated with cerebral ischemia. Ischemia means deficient blood supply. The compounds of the invention can be administered to a stroke patient either before, during, or after the stroke, but preferably are administered to a stroke patient during the time period between initiation and completion of the stroke. Stroke initiation refers to the onset of cerebral ischemia. This typically would be associated with a disruption of blood flow. Exemplary events of this type would include, among others, thromboses, atherothromboses, emboli, thromboemboli, hemorrhages, and blood hyperviscosity. Completion of the stroke refers to the time at which there is no further extension of the area of tissue damage resulting from the cerebral ischemia. The time of completion of the stroke will vary depending on the age and characteristics of the patient, the cause of the ischemia, and medical or surgical treatments given to the patient.

The term "patient" used herein is taken to mean any mammalian patient. Patients specifically intended for treatment with the method of the invention include humans, as well as nonhuman primates, sheep, horses, cattle, pigs, dogs, cats, rabbits, guinea pigs, rats and mice, as well as the organs derived or originating from these hosts.

The invention further encompasses a pharmaceutical preparation for intravascular infusion, consisting of a sterile solution containing either L-arginine or another substrate for NO synthase, such as an analog of L-arginine. "Sterile" denotes a total absence of microorganisms. The preparation is formulated so that it may be administered to a patient in a rapid intravascular infusion. For this reason, the viscosity of the preparation is not high. In a preferred embodiment, the preparation is either isotonic or hypotonic, and contains less than 5 grams of glucose per 100 milliliters of solution.

Other features and advantages of the invention will be apparent from the following descriptions, and from the claims.

DETAILED DESCRIPTION

The drawings will first be briefly described.

Drawings

THERAPEUTIC USE IN STROKE

Figure 1:
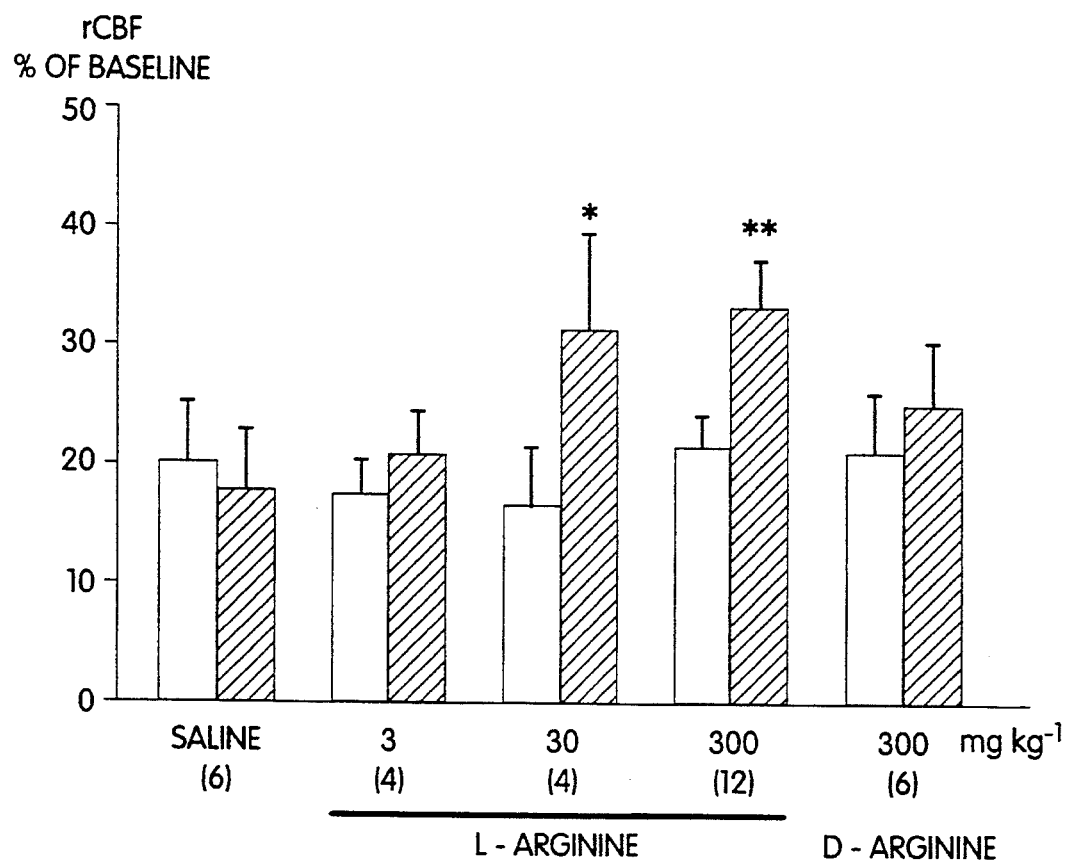
FIG. 1 is a bar graph illustrating the effects of intravenous administration of saline, of three different concentrations of L-arginine, or of D-arginine on regional cerebral blood flow (rCBF) after an experimentally induced stroke in spontaneously hypertensive rats. L-arginine infusion ($\geq 30$ mg/kg, i.v.), but not D-arginine infusion, increased rCBF.

For use in the treatment of stroke, the NO-releasing compounds of the invention are administered to stroke patients to limit the extent of stroke-associated infarcts. Stroke is a complex disease process, with as yet poorly defined pathogenic mechanisms. The means by which the methods and preparation of the invention exert beneficial effects on residual stroke damage is not known.

The method will be advantageous for the treatment of various clinical presentations of stroke patients. The treatment of the invention may be administered to patients at risk of stroke occurance, such as those suffering episodes of transient ischemic attacks. In most patients, administration of the treatment preferably is begun shortly after the initiation of the stroke, since early intervention will maximize the extent of potentially salvageable penumbral tissue. Treatment may be initiated, however, at any point in time prior to the completion of the infarction process, as assessed both on the basis of physical findings on neurological examination of the patient, as well as on the basis of imaging studies such as computed tomography or magnetic resonance imaging. In certain instances, the methods of the invention may be used to treat a patient after the completion of a stroke episode.

ADMINISTRATION

The compounds of the invention may be administered in any manner which is medically acceptable. This may include injections, by parenteral routes such as intravenous, intraarterial, subcutaneous, intramuscular, intraperitoneal, intraventricular, intraepidural, or others, as well as oral, nasal, ophthalmic, rectal, or topical. Sustained release administration is also specifically included in the invention, by such means as depot injections or erodible implants. The preferred means of administration are by intravenous injection, either as a bolus injection or as an infusion.

Nitric oxide may be administered in any manner which will deliver free NO to brain tissues, producing NO concentrations in the brain of at least 0.01 $\mu M$, and preferably between 0.001 and 1000 $\mu M$. Such a manner may include inhalation of nitric oxide gas, injection of a solution containing dissolved NO, or implantation of a device which releases NO. The NO-releasing compounds of the invention may be administered to patients at between about 10 and about 1000 mg/kg. For L-arginine and for L-arginine analogs, a preferred dosage range is from about 10 to about 500 mg/kg, administered parenterally. Most preferably, the L-arginine analogs are administered at dosages of from about 20 to about 350 mg/kg.

The compounds of the invention are formulated for intravascular administration as sterile solutions with appropriate additions to make pharmaceutically acceptable preparations. Components of the solution might include salts, buffers, preservatives, antioxidants, osmotic agents, fibrinolytic compounds, or complementary therapeutic agents.

Nitric Oxide-Releasing Compound Dilates Cerebral Arterioles and Increases Blood Flow during Experimental Stroke Methods Laser-Doppler Flowmetry 36 male spontaneously hypertensive rats (SHR; 280–340 g; Charles River Labs, Wilmington, Mass.) were subjected to common carotid artery (CCA)/middle cerebral artery (MCA) occlusion as described previously (Brint et al., *J. Cereb. Blood Flow Metab.* 8:474–485, 1988). Briefly, anesthesia was induced and maintained by halothane, 3 and 0.5% respectively, along with 70% nitrous oxide and balance oxygen in ventilated animals. The MCA was occluded by a metallic clip (Zen clip, Ohwa Tsusho) just distal to the rhinal fissure within 1 min after CCA occlusion.

rCBF was monitored continuously (BPM 403A, TSI Inc.) as described (Koketsu et al., *J. Cereb. Blood Flow Metab.* 12:613–620, 1992) through a craniotomy over dorsolateral cortex [4–6 mm lateral, −2 mm to 1 mm rostral to bregma; the transitional zone from several to mildly ischemic in this model (Jacewicz et al., *J. Cereb. Blood Flow Metab*, 10:903–913, 1990)].

Closed Cranial Window 20 male Sprague Dawley rats (280–330 g; Charles River Labs) were anesthetized with sodium pentobarbital (50 mg kg$^{-1}$ ip, plus 10 mg kg$^{-1}$ ip hourly), paralyzed (pancuronium bromide 0.5–1.0 mg iv) and mechanically ventilated with O2 supplemented room air; end-tidal $P_{CO2}$ was monitored continuously (Novametrix Medical Systems, Wallingford, Conn.).

Pial vessels were visualized using an intravital microscope (200×magnification; Leitz, Germany). A window was placed over the left parietal cortex. The space under the window was then filled with mock CSF (Levasseur et al., *Stroke* 6:308–317, 1975) equilibrated at 37° C. with a gas containing 10% oxygen, 5% CO2 and balance nitrogen. Measurements were taken (VIA-100, Boeckler Instruments) after the image was transposed onto a video monitor (Dage MTI Inc., CCD-72 series, Michigan City, Ind.).

Arterial blood pressure and blood gases were monitored and rectal temperature was maintained at 37° C. in all experiments.

Chemicals

L- or D-Arginine hydrochloride (Sigma Chemical Co., St. Louis, Mo.) was dissolved in distilled water and adjusted to pH 7.0 with sodium hydroxide. N$^G$-nitro-L-arginine methyl ester (L-NAME; Sigma) was dissolved in mock CSF immediately prior to use.

Results

There were no significant differences in MABP, pHa, plasma glucose, paO2, paCO2, rectal temperatures between treatment groups when rCBF or pial vessel diameter were monitored (data not shown).

As shown in FIG. 1, L-Arginine infusion ($\geq 30$ mg/kg, iv) but not D-arginine increased rCBF in the MCA territory after combined CCA/MCA occlusion in SHR. After 15 mins of stable rCBF recordings, the CCA/MCA was occluded as described and rCBF measured 2 and 5 mins later (clear bars). L-or D-Arginine or saline was then administered at a constant rate of 100 μl $kg^{-1} min^{-1}$ for 10 mins (Harvard infusion pump, Harvard Bioscience, South Natick, Mass.) at the dosages indicated. Post-infusion rCBF, determined at 15 min intervals for the next 105 mins, is expressed as the mean of these determinations (filled bars). Data are expressed as percentage of baseline rCBF prior to vessel occlusion (mean±SEM with number of animals in parentheses). rCBF 2 and 5 mins after CCA/MCA occlusion was 20±5.2% for the saline group, and did not differ between treatment groups. *$p<0.05$ and **$p<0.01$ as compared to pre-infusion rCBF, determined by paired Student's t test.

CCA/MCA occlusion reduced rCBF by approximately 80% of baseline (FIG. 1). L-Arginine, 30 and 300 mg $kg^{-1}$ increased rCBF following occlusion whereas saline, 3 mg $kg^{-1}$ of L-arginine or D-arginine did not. The findings do not appear to depend upon the choice of anesthetic. When pentobarbital (65 mg $kg^{-1}$) was used instead of halothane/nitrous oxide, L-arginine (300 mg $kg^{-1}$) also increased rCBF from 29±6 to 44±8% (n=4, $p<0.05$ by paired Student t test).

Figure 2:
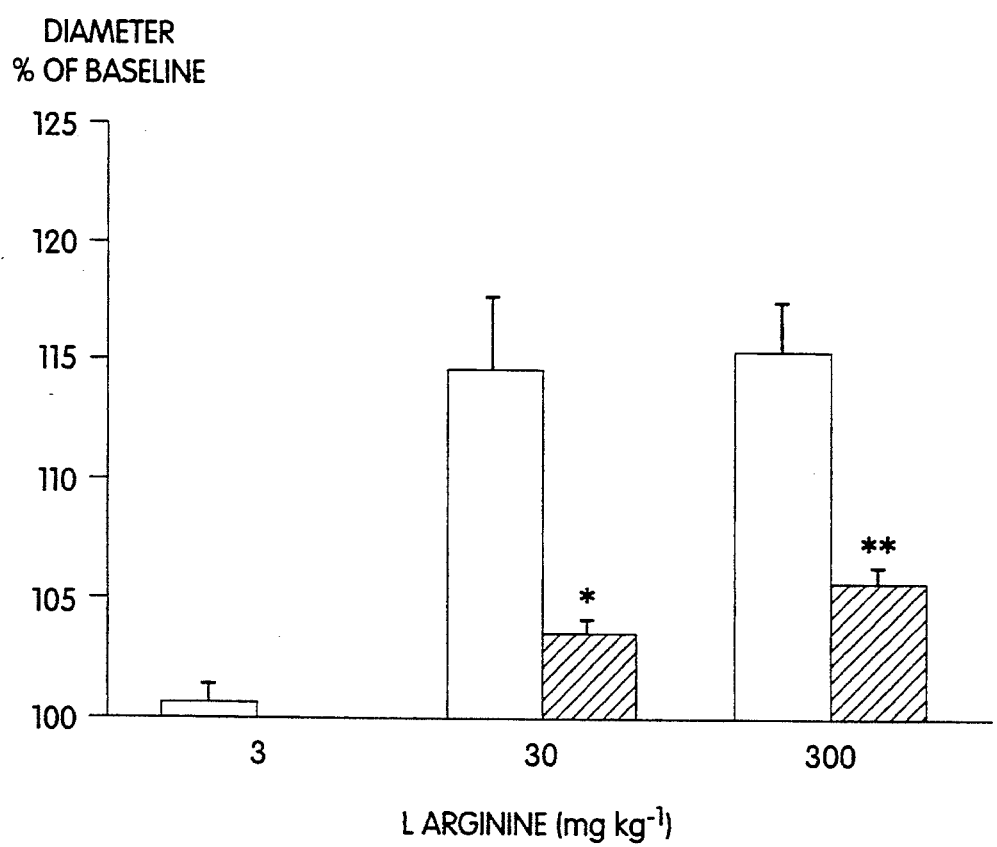
FIG. 2 is a bar graph depicting the dilation of surface blood vessels of rat brains after treatment with L-arginine (open bars). The dilation of vessels after L-arginine treatment was significantly reduced by topical treatment with L-NAME (hatched bars).

L-Arginine (30 and 300 but not 3 mg $kg^{-1}$) increased pial vessel diameter (FIG. 2). Topical L-NAME (1 μM) significantly attenuated these responses in Sprague Dawley rats. Baseline diameters were measured after equilibration period of 30 mins through a closed cranial window. Pial vessel diameters (1-3 arterioles per animal) were measured 30 mins following L-arginine iv infusion (3, 30, or 300 mg $kg^{-1}$ over 10 mins; clear bars). In some animals, L-NAME (1 μM) was applied topically 20 mins prior to L-arginine infusion (hatched bars). Data are expressed as percentage of baseline diameter. L-NAME superfusion (1 μM) by itself did not change pial vessel diameter (100±1.2%, n=7). Baseline diameters (mean±SEM in μm) were 42±2.7 for 3 mg $kg^{-1}$ (n=3), 49±3.7 for 30 mg $kg^{-1}$ (n=5), and 40±4.1 for 300 mg $kg^{-1}$ (n=5) of L-arginine; 34±7.0 and 40±9.9 for 30 (n=3) and 300 mg/kg (n=4) L-arginine with L-NAME pretreatment groups, respectively. Error bars denote SEM. *$p<0.05$ and **$p<0.01$, as compared to L-arginine infusion alone by unpaired Student's t test.

Nitric Oxide-Releasing Compound Decreases Infarct Size Following Experimental Stroke

MATERIALS AND METHODS

Middle cerebral artery occlusion

Sixty male SHR (260-320 gms; Charles River Laboratories, Wilmington, Mass.) were housed under diurnal lighting conditions and allowed food and water ad libitum.

Infarction volume was determined 24 hrs after middle cerebral artery (MCA) occlusion in two models. In model 1, both the right distal MCA and the ipsilateral common carotid artery (CCA) were occluded according to Brint et al., J. Cereb. Blood Flow Metab. 8:474-485, 1988; Koketsu et al., J. Cereb. Blood Flow Metab., in press. In model 2, the right proximal MCA was occluded according to Tamura et al., J. Cereb. Blood Flow Metab. 1:53-60, 1981. In both, 3 and 1 percent halothane was used for induction and maintenance of anesthesia, respectively along with 70 percent nitrous oxide/balance oxygen. Rats were mechanically ventilated through an endotracheal tube (PE-240 polyethylene tubing). Respiratory parameters were adjusted as needed in order to maintain normal arterial blood gases. Arterial blood pressure was continuously monitored as previously described (Kano et al., J. Cereb. Blood Flow Metab. 11:628-637, 1991). Arterial pH, $P_{CO2}$, $P_{O2}$ (178 pH/Blood Gas Analyzer, Ciba-Corning, Medfield, Mass.), hematocrit, and plasma glucose (Accu-Chek IIm, Boehringer Mannheim Diagnostics, Indianapolis, IN) were sampled intermittently. Rectal temperature was maintained normothermic by a Homeothermic Blanket Control Unit (Harvard Apparatus) preset to 37° C.

The distal (model 1) or proximal (model 2) segment of the MCA was exposed as described elsewhere (Brint et al., J. Cereb. Blood Flow Metab. 8:474-485, 1988; Tamura et al., J. Cereb. Blood Flow Metab. 1:53-60, 1981) with minor modifications. Briefly, a 1 cm skin incision was placed approximately midway between the right outer canthus and anterior pinna. After removal of the zygomatic arch, the temporalis muscle was incised and retracted to expose the infratemporal fossa. A craniotomy (3 mm diameter) was created at the juncture of the zygoma and squamous bone (model 1) or just anterior to the foramen ovale (model 2) by a dental drill cooled with saline. The dura mater was opened with a fine curved needle. In model 1, the MCA was electrocoagulated medial to the rhinal fissure (2 mm segment) after ligating the right CCA with two 4-0 silk sutures. The coagulated segment was then transected. In model 2, the MCA was ligated twice with 10-0 monofilament at the medial edge of the olfactory tract and transected. Each model was performed by a single investigator. After surgery, the rats were returned to their cages, allowed free access to food and water and given a single injection of Cefazolin, 50 mg. i.m.

Twenty-four hours later, rats were killed by decapitation and infarct volume was measured in 2 mm brain slices previously incubated with 2 percent 2, 3,5-triphenyltetrazolium chloride monohydrate (TTC) as described previously (Kano et al., J. Cereb. Blood Flow Metab. 11:628-637, 1991; Koketsu et al., J. Cereb. Blood Flow Metab., in press).

Experimental protocol

Three hundred milligrams of L- or D-arginine (Sigma Chemical Co., St. Louis, Mo.) were dissolved in 1 ml of distilled water. Both solutions were adjusted to pH 7.0 with sodium hydroxide. Rats received L- or D-arginine in a dose of 300 mg/kg i.p. at 16 and 3 hours before and 5 and 120 minutes after MCA occlusion or the same volume of saline.

Statistical analysis

Data are expressed as the means±SEM. One way analysis of variance (ANOVA) followed by Tukey's test was used to compare the data among the three groups in model 1. In model 2, an unpaired Student's t test was used to compare the two groups. Statistical significance was accepted at the 95% confidence level ($p<0.05$).

RESULTS

Physiologic variables

Physiologic variables at the time of MCA occlusion are shown in Table 1 and are not significantly different between groups in either model. Neither L- nor D-arginine affected body temperature during anesthesia (Table 1) or after 2 hours following MCA occlusion (36.7°±0.2° and 36.9°±0.2° C. respectively)

Infarct volume

Infarct volumes after L-arginine were smaller than after saline or D-arginine by 31% ($p<0.05$) and 39% ($p<0.01$), respectively, in model 1 (Table 2). In model 2, L-arginine decreased infarct size in both striatum (28%, p<0.05) and neocortex (11%, p<0.05) as compared to the saline treated group.

Infarct areas were lower in every brain slice in model 1 after L-arginine treatment as compared with saline, although statistically significant differences were detected in slice 5 only (p<0.01). Infarction areas on the seven coronal slices in model 1 are presented in FIG. 3, and those on the slices in model 2 (neocortex+striatum) are presented in FIG. 4. Slice #1 is the most rostral. Data are presented as means±SEM. *p<0.01 as compared to the saline treated group; **p<0.01 as compared to the D-arginine treated group.

Figure 3:
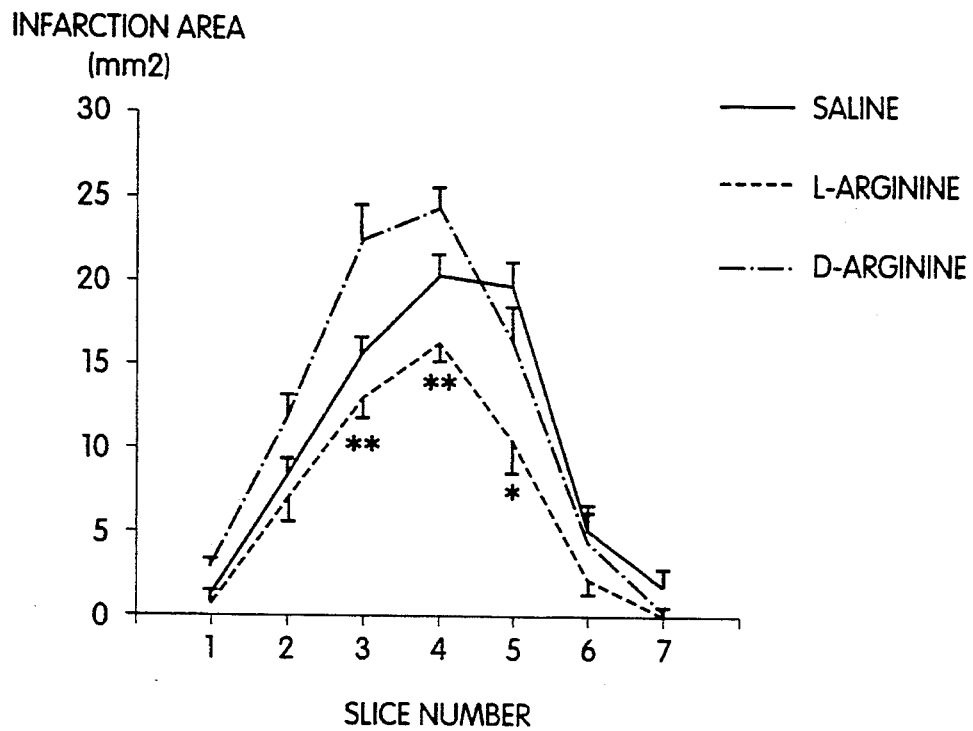
FIG. 3 is a graph of the infarction areas of seven consecutive slices of the coronal brain area of rats following ligation of the distal middle cerebral artery plus the ipsilateral common carotid artery. Treatment with L-arginine, but not with D-arginine, significantly decreased the infarct size.
Figure 4:
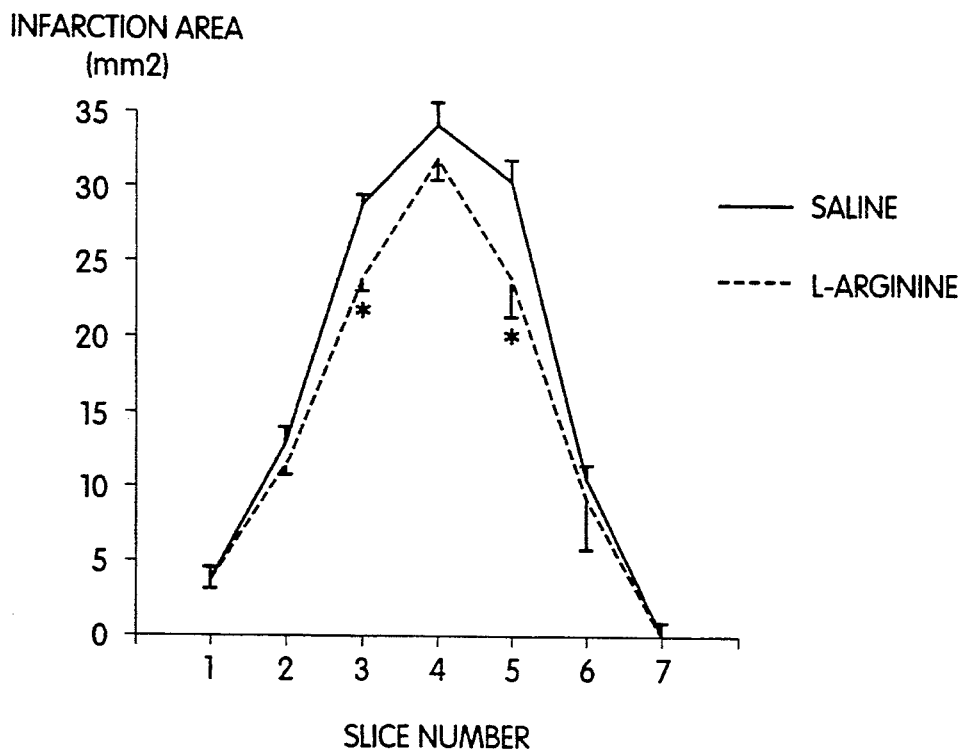
FIG. 4 is a graph of the infarction areas of seven consecutive slices of the coronal brain area of rats following ligation of the proximal middle cerebral artery. Treatment with L-arginine significantly decreased the infarct size of slices marked on the graph with *.

Infarct areas were significantly reduced in slices 3 and 4 (p<0.01) when the effects of L- and D-arginine were compared (FIG. 3). In model 2, treatment with L-arginine significantly reduced infarct areas in slices 3 (p<0.01) and 5 (p<0.01) as compared with saline (FIG. 4).

Other Embodiments

Persons skilled in the pharmaceutical arts will recognise that many other NO-releasing compounds may be used in the stroke treatments of the invention, and are intended to be included within the scope of the invention. For example, the invention encompasses the compounds described in U.S. Pat. Nos. 4,954,526 and 5,039,705 to Keefer, the specifications of which are herein incorporated by reference.

Equivalents

It should be understood that the foregoing description of the invention is intended merely to be illustrative by way of example only and that other modifications, embodiments, and equivalents may be apparent to those skilled in the art without departing from its spirit.

TABLE 1

| Physiologic variables before MCA occlusion | | | | | |
|---|---|---|---|---|---|
| | | | Model 1 | | Model 2 |
| | saline | L-arginine | D-arginine | saline | L-arginine | |
| | (n = 10) | (n = 19) | (n = 10) | (n = 10) | (n = 11) |
| MABP (mmHg) | 138 ± 5 | 137 ± 3 | 131 ± 4 | 133 ± 5 | 132 ± 4 |
| $P_{CO_2}$ (mmHg) | 36 ± 1 | 37 ± 1 | 36 ± 1 | 33 ± 2 | 34 ± 1 |
| $P_{O_2}$ (mmHg) | 146 ± 7 | 141 ± 4 | 133 ± 8 | 170 ± 9 | 154 ± 11 |
| pH | 7.41 ± 0.01 | 7.39 ± 0.01 | 7.40 ± 0.01 | 7.45 ± 0.02 | 7.44 ± 0.02 |
| BS (mg/dl) | 126 ± 6 | 124 ± 4 | 109 ± 8 | 132 ± 4 | 130 ± 4 |
| Hct (%) | 41 ± 1 | 41 ± 1 | 41 ± 1 | 44 ± 1 | 46 ± 1 |
| BT (°C.) | 37 ± 0.1 | 37 ± 0.1 | 37 ± 0.1 | 37 ± 0.1 | 37 ± 0.1 |
| TMT (°C.) | 36 ± 0.5 | 36 ± 0.3 | 37 ± 0.2 | N/A | N/A |

Values are means±SEM. There are no significant inter-group differences in these physiologic variables in either model. MABP, mean arterial blood pressure; BS, plasma glucose; Hct, hematocrit; BT, TMT, body temperature and temporalis muscle temperature, respectively; N/A, not available.

TABLE 2

| Infarct volumes | | |
|---|---|---|
| Model 1 | | |
| Treatment | n | Infarct Volume (mm³) |
| saline | 10 | 147 ± 12 |
| L-arginine | 19 | 101 ± 9* |
| D-arginine | 10 | 167 ± 14 |
| Model 2 | | |
| Treatment | Neocortex | Striatum |
| saline | 10 | 193 ± 7 | 47 ± 5 |
| L-arginine | 11 | 171 ± 8** | 34 ± 3** |

Values are means±SEM. *Different from saline treated group (p<0.05) and D-arginine treated group (p<0.01) by one-way ANOVA, Tukey's test. **Different from saline treated group (p<0.05) by unpaired Student's t test.

We claim:

1. A method for treatment of an ischemic stroke patient, comprising administering intraveneously to said patient an effective amount of a nitric oxide-releasing compound for treating the ischemic stroke.

2. The method of claim 1, wherein the nitric oxide-releasing compound is L-arginine.

3. The method of claim 1, wherein said nitric oxide-releasing compound is administered to the patient during the time period between initiation and completion of the stroke.

4. A method for treatment of an ischemic stroke patient, comprising administering intravenously to said patient an effective amount for treating the stroke of a compound which is a substrate for nitric oxide synthase.

* * * * *